United States Patent [19]
Davies

[11] Patent Number: 4,562,737
[45] Date of Patent: Jan. 7, 1986

[54] ULTRASONIC TESTING
[75] Inventor: David H. Davies, Cleveland, England
[73] Assignee: British Steel Corporation, England
[21] Appl. No.: 524,343
[22] Filed: Aug. 18, 1983
[30] Foreign Application Priority Data Aug. 19, 1982 [GB] United Kingdom ............... 8223954
Oct. 15, 1982 [GB] United Kingdom ............... 8229604

[51] Int. Cl.⁴ ........................................... G01N 29/04
[52] U.S. Cl. ........................................ 73/622; 73/633; 73/644
[58] Field of Search ............... 73/622, 644, 641, 637, 73/638, 588, 633

[56] References Cited
U.S. PATENT DOCUMENTS

| 3,169,393 | 2/1965 | Stebbins | 73/622 |
| 3,255,626 | 6/1966 | Van der Veer | 73/644 |
| 3,910,104 | 10/1975 | Davies | 73/641 |
| 4,375,167 | 3/1983 | Nusbickel et al. | 73/644 |

Primary Examiner—Anthony V. Ciarlante
Attorney, Agent, or Firm—Bacon & Thomas

[57] ABSTRACT

The invention provides apparatus for ultrasonically testing the edges and/or the body of a metallic workpiece, utilizing water as a coupling medium between ultrasonic transducers and a metallic product moving relative to the testing apparatus along a predetermined pathway; which apparatus comprises guide means defining the pathway to be followed by the metal product, one or more reservoirs being the pathway each incorporating a top opening through which water can overflow to contact successive parts of the piece to be tested, located thereabove and a plurality of ultrasonic transducers located in one or more groups within the reservoir or reservoirs and directed towards the edge or body of the piece to be tested so that they may be static, adjustable transverse to the direction of movement of the product along the pathway, or reciprocate in a sinusoidal manner to traverse all or part of the pathway.

3 Claims, 8 Drawing Figures

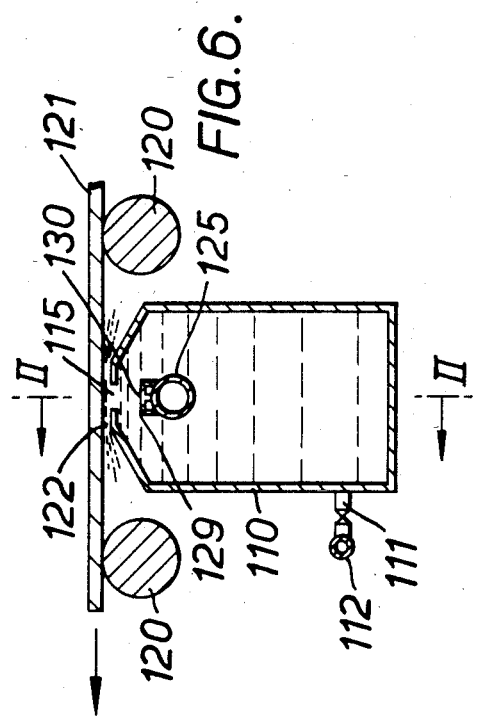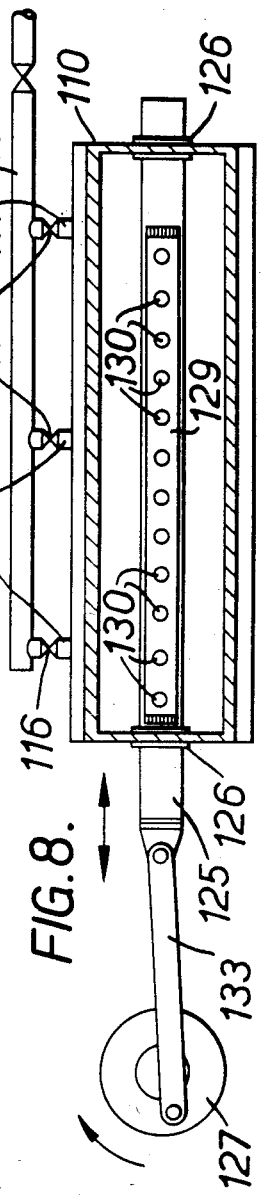

ULTRASONIC TESTING

This invention relates to ultrasonic testing, and more particularly to the ultrasonic testing of the edges and/or the bodies of metallic products such as steel plates or steel pipes. Where the edges of steel plates are to be subjected to welding, such as in the production of pipe by the welding of separate plates together, or the welding of opposite edges of spirally wound strip together, detailed inspection of the opposed welding edges is necessary to ensure good quality for welding so as to reduce to a minimum welding faults during production of the pipe.

Again, the opposed end edges of tubes and pipes, which are to be connected together by welding for example, need to be quality inspected.

It has previously been proposed to test the bodies of products of this kind by moving the product along a line of travel adjacent to a water reservoir such that water from the reservoir contacts successive parts of the product to be tested. At the same time there is provided in the reservoir a beam carrying a plurality of ultrasonic transducers spaced therealong. In practice as the product is moved past the reservoir the beam is reciprocated axially by means of a pneumatic or hydraulic piston and cylinder set, whilst the transducers are activated to transmit pulses into the product and receive reflections thereof from the product using the reservoir water as an accoustic coupling medium.

Although apparatus of this kind (hereinafter called "apparatus of the kind referred to") is capable of valuable inspection work with respect to products such as steel plate, it does incorporate a problem in that the beam reciprocation does not in practice perform at constant velocity so that a full area inspection of the product as it passes is not always exactly obtained.

It is an object of the present invention to provide for the effective and convenient testing of metallic products.

According to the invention there is provided apparatus for ultrasonically testing the edges and/or body of a metallic work piece, utilising water as a coupling medium between ultrasonic transducers and a metallic product moving relative to the testing apparatus along a generally predetermined pathway; which apparatus comprises guide means defining the pathway to be followed by the metal product, one or more reservoirs below the pathway each incorporating a top opening though which water can overflow to contact successive parts of the piece to be tested located thereabove, and a plurality of ultrasonic transducers located in one or more groups within the reservoir or reservoirs and directed towards the edge or body of the piece to be tested so that they may be static or reciprocate in a sinusoidal manner to traverse all or part of the pathway and may be adjustable transverse to the direction of movement of the product along the pathway in order to change the position of the area of inspection.

In one embodiment of the invention there is provided apparatus for simultaneously ultrasonically testing the opposed edges of a metallic workpiece utilising water as a coupling medium between ultrasonic transducers and a metallic product moving relative to the to the testing apparatus along a predetermined pathway, which apparatus comprises guide means defining the pathway to be followed by the metal product; one reservoir for water having a top opening and so arranged in relation to the pathway as to be immediately below one edge of the metal product, a second reservoir for water having a top opening and moveably mounted on a carriage way transverse to the pathway so as to be capable of positioning immediately below the opposed edge of the metal product, water supply means to the two reservoirs arranged to provide a continuing supply of water thereto so as to overflow in use from the top of the reservoir to contact with the metal product passing along the pathways thereabove, and a plurality of ultrasonic transducers located within each reservoir and directed towards the edge of the metal product passing thereacross. The invention includes within its scope a method of ultrasonic testing using the apparatus herein defined.

Another embodiment of the invention provides apparatus of the kind referred to including means for reciprocating the beam in operation of the arrangement wherein said means is arranged to provide a sinusoidal drive for the beam.

The means for providing the sinusoidal drive for the beam may comprise a crankshaft drive.

In a preferred embodiment the water reservoir has a narrow overhead opening through which, in operation, water is allowed to escape. In such an arrangement the product is arranged such that its path of travel lies across the overhead opening of the reservoir whereby the product impinges upon escaping water from the reservoir as it passes thereacross.

Previous proposals for the use of a pneumatic cylinder for example to drive the reciprocating beam theoretically involve the beam in a movement with constant velocity so that each ultrasonic transducer describes a saw-tooth inspection pattern along the length of the product in operation. We have found that in practice however such a cylinder does not provide constant velocity, and that in addition, at the beginning and end of each stroke there is an inevitable total pause in movement of the beam. The result of this is that a significant area of the product is not inspected in operation and the saw-tooth pattern described by the transducers is considerably distorted.

By means of a drive according to the invention each transducer on the beam describes a sinusoidal inspection path along the surface of the workpiece capable of providing a true and even test pattern across the product.

In order that the invention may be more readily understood three embodiments thereof will now be described by way of example with reference to the accompanying drawings in which:

FIG. 6 is a sectional end view of apparatus for ultrasonically testing a rolled steel plate, taken on the line I—I of FIG. 7;

FIG. 8 is a sectional plan view of the apparatus, taken on the line III—III of FIG. 7.

Figure 1:
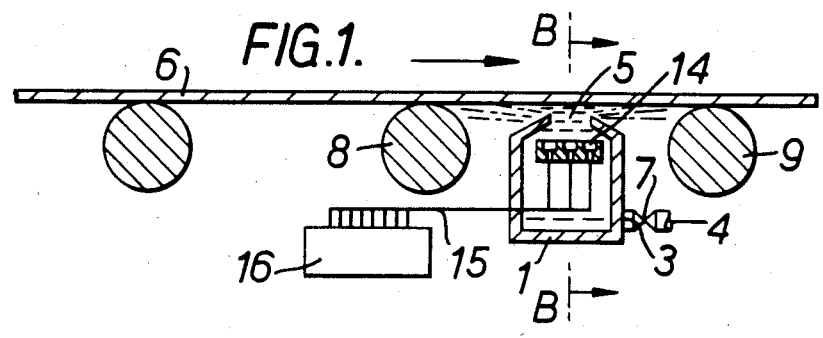
FIG. 1 is a schematic sectional side elevation on the line AA of FIG. 3 of apparatus for ultrasonically testing the edges of steel plates.
Figure 2:
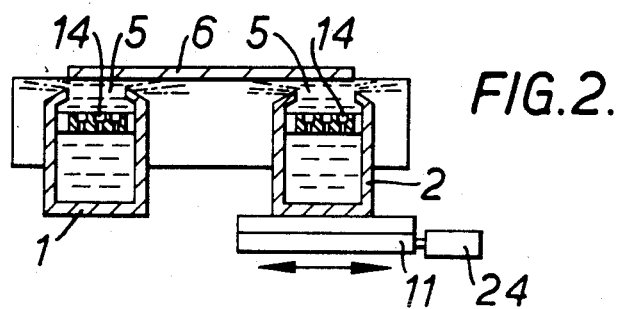
FIG. 2 is a schematic front elevation along the line BB of FIG. 1.
Figure 3:
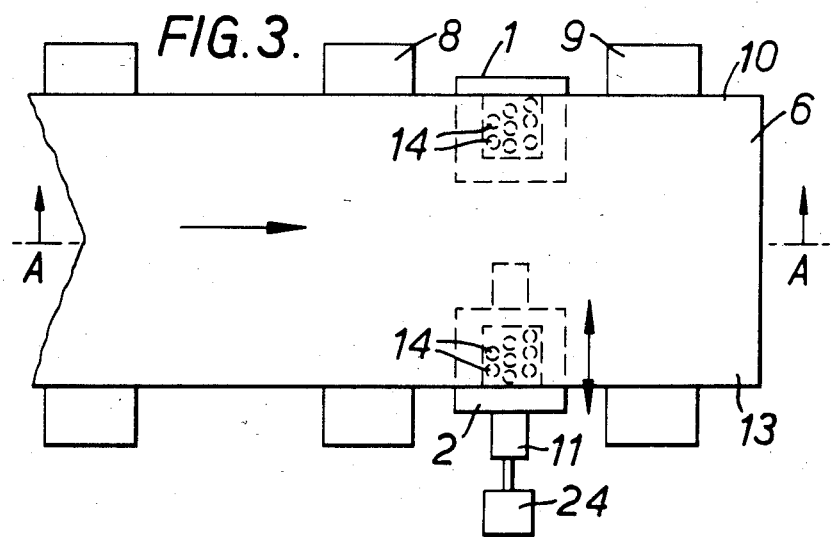
FIG. 3 is a schematic plan view of the apparatus of FIG. 1.

In FIGS. 1, 2 and 3 of the drawings water reservoirs 1 and 2 have inlets 3 continuously supplied with water from the pipes 4. Each reservoir has an upper or top opening 5 through which water wells up to contact and provide accoustic coupling with a steel plate workpiece 6, before draining away down the outside of the reservoir, whence it can be collected and recycled, after filtration if necessary, to the supply pipes 4. The water inlets are controlled by valves 7 so as to give a desired even flow of water through the openings.

The two reservoirs are situated between two sets of rollers 8 and 9 of a roller table along which the steel plates 6 can be driven.

A plate is shown travelling between these two rollers, the top of the reservoirs is just below the lower face of the plate as it passes, and sufficiently close so that the water welling up from the upper openings thereof contacts the plate in a continuously replenished pool.

It is to be noted that one reservoir 1 is located beneath one side edge 10 of the steel plate 6, whilst the other reservoir 2 is mounted on a carriage 11 moveable by means of a motor 24 transverse to the direction of travel of the plate so that it can be located below the other side edge 13 of the plate or indeed the opposed side edge of a plate of different width.

Within each reservoir is located a plurality of ultrasonic transducers 14 connected electrically for the transmission of ultrasonic pulses and the receipt of echoes thereof from the plate. The transducers are connected by insulated electrical connections 15 to a control unit 16 which actuates the transducers and monitors their response. The control unit detects the presence of a defect in the respective edge of the plate in known manner.

Figure 4:
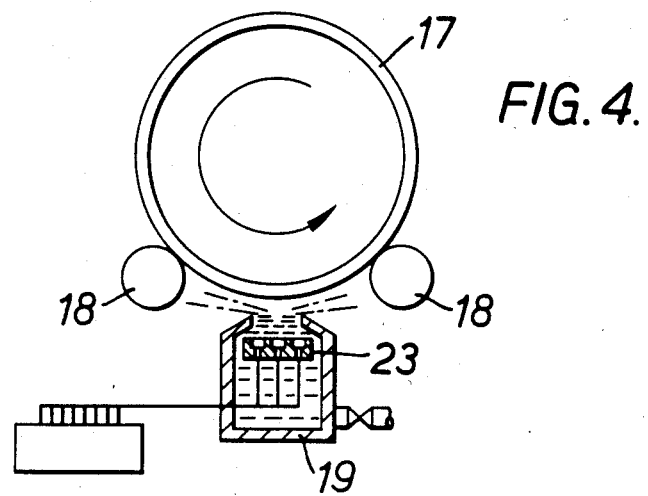
FIG. 4 is a schematic front elevation of apparatus for ultrasonically testing the edges of steel tubes.
Figure 5:
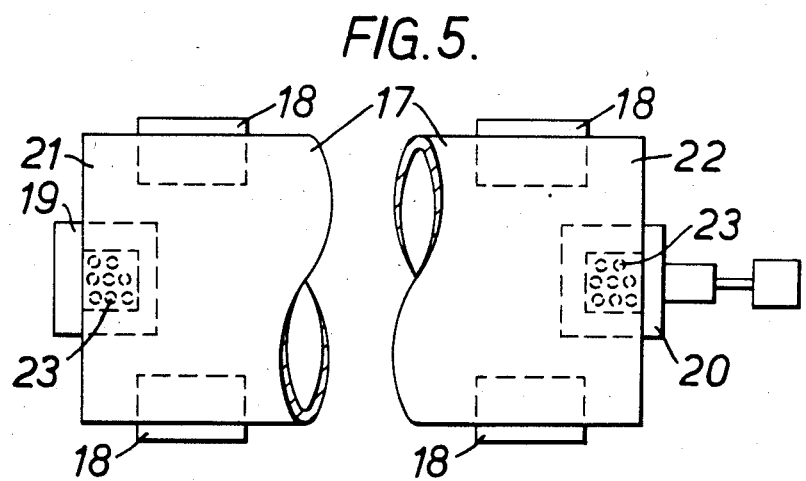
FIG. 5 is a schematic plan view of the apparatus of FIG. 4

The second embodiment of the invention illustrated in FIGS. 4 and 5 utilises the same principles of the first embodiment adapted to the testing of the edges of a tube 17.

In this case, as can be seen, the tube 17 is rotated on rollers 18 and two reservoirs 19 and 20 are located below each of the two edges 21 and 22 of the tube so that the edges are tested by ultrasonic devices 23 located within the reservoirs in like manner to the edges of the plate illustrated in FIGS. 1 to 3.

Figure 7:
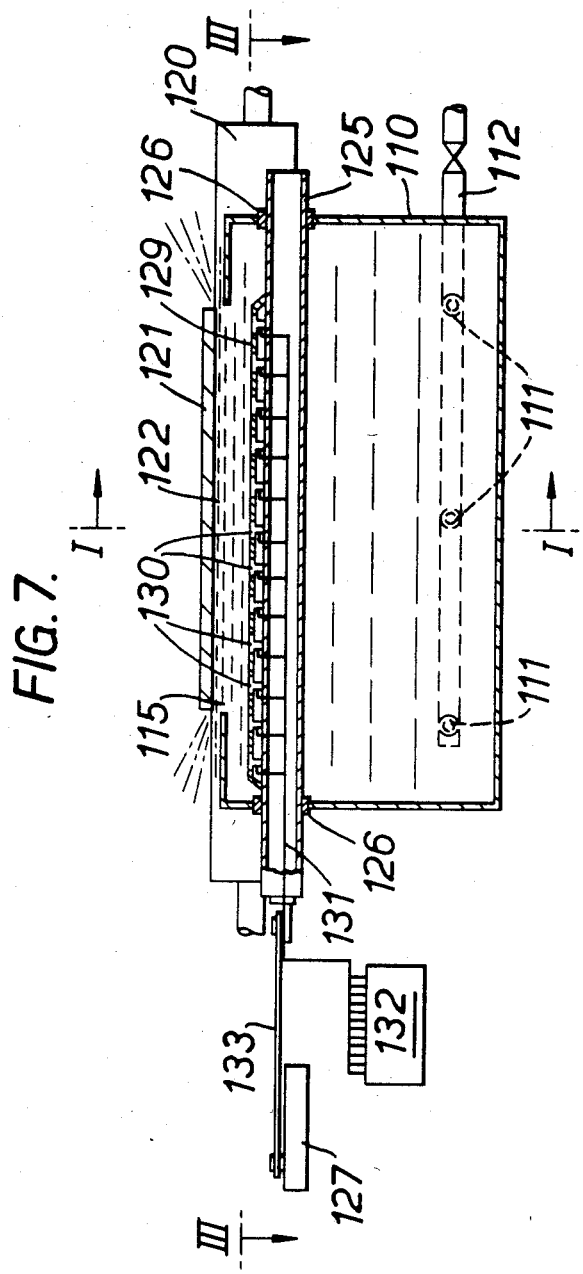
FIG. 7 is a sectional side view of the apparatus, taken on the line II—II of FIG. 6.

In FIGS. 6, 7 and 8, a tank 110 has three inlets 111 continuously supplied with water from a pipe 112. The tank has a longitudinal slot 115 in its top through which water wells up before draining away down the outside of the tank, after which it can be collected and recycled, after filtration if necessary, to the supply pipe 112. The inlets 111 are spaced along the tank and are controlled by individual valves 116 to give an approximately even flow of water along the length of the slot 115.

The tank is situated between two rollers 120 of a roller table along which steel plates can be driven. A plate 121 is shown travelling across these two rollers. The top of the tank containing the slot 115 is just below the lower face of the plate as it passes, and sufficiently close that the water welling up from the slot 115 contacts the plate across its whole width in a continuously replenished pool 122.

Directly under the slot 115 and parallel with it the tank 110 carries a beam in the form of a stainless steel tube 125 which extends through opposite ends of the tank through water seals 126 which permit the tube 125 to slide axially. A crankshaft drive, comprising a crank wheel 127 and link lever 133, is connected to one end of the tube and is arranged to reciprocate the tube in the tank.

Along the top of the tube 125 is affixed an external duct 129 carrying an array of ultrasonic transducers 130 directed through the slot 115. The length of the array of the transducer is greater than the width of the plate by an amount which is sufficient to ensure that at the extreme positions of the tube 125 during its axial reciprocation neither edge of the plate overreaches either end of the array of transducers. The relative positions and orientations of the transducers 130, the slot 115 and the plate 121 are such that ultrasonic energy pulses emitted by each transducer are reflected back to the same transducer from the plate.

The transducers 130 are individually connected by insulated electrical connections 131 to a control unit 132, which actuates the transducers and monitors their response to ultrasonic energy reflected from the plate 121. The control unit 132 detects the presence of a defect in the plate in known manner.

The invention can be used in other manners than that specifically described above in relation to FIGS. 6, 7 and 8. Thus, it is possible to inspect a tube rather than a plate by aligning the tube lengthways over the slot and then rotating the tube until its whole circumference has passed over the slot.

In operation the array of ultrasonic transducers 130 describe a succession of evenly spaced sinusoidal inspection paths over the surface of the product, ensuring good full area inspection thereof.

It will be understood that in the arrangement of FIGS. 1 to 5 both reservoirs 1 and 2 can be arranged for movement transverse to the direction of travel of the plate, so that, for example, wander of the edges of the plate during travel can be accommodated at both sides. Means may be provided, such as edge detecting switches, to enable the or each reservoir to follow the associated plate edge.

By means of the invention we have provided a convenient, effective and simple means for testing metal products such as plates or tubes of different width or length.

I claim:

1. Apparatus for ultrasonically testing a metallic workpiece, utilising water as a coupling medium between ultrasonic transducers and a metallic product moving relative to the testing apparatus along a generally predetermined pathway; which apparatus comprises guide means defining the pathway to be followed by the metal product, one or more reservoirs below the pathway each incorporating a top opening through which water can overflow to contact successive parts of the piece to be tested located thereabove, and a plurality of ultrasonic transducers located in one or more groups within the reservoir or reservoirs and directed towards the testpiece, at least one of the groups of transducers being connected to a beam, said beam being connected to a crank wheel for reciprocating said beam along a linear path such that a sinusoidal testing path is described along the length of the workpiece as the workpiece passes over the reciprocating beam.

2. Apparatus as claimed in claim 1 for ultrasonically testing the opposed edges of a metallic workpiece utilising water as a coupling medium between ultrasonic transducers and a metallic product moving relative to the testing apparatus along a predetermined pathway, which apparatus comprises guide means defining the pathway to be followed by the metal product; one reservoir for water having a top opening and so arranged in relation to the pathway as to be immediately below one edge of the metal product, a second reservoir for water having a top opening and moveably mounted on a carriage way directed transverse to the pathway so as to be capable of positioning immediately below the opposed edge of the metal product, water supply means to the two reservoirs arranged to provide a continuing supply of water thereto so as to overflow in use from the top of the reservoir to contact with the metal product passing along the pathway thereabove, and a plurality of ultrasonic transducers located within each reservoir and directed towards the edge of the metal product passing thereacross.

3. Apparatus as claimed in claim 2 wherein the second reservoir is moveable on the carriage way by means of a control motor.

* * * * *